United States Patent
Heneghan et al.

[11] Patent Number: 5,983,902
[45] Date of Patent: Nov. 16, 1999

[54] METHOD OF MANUFACTURING A COSMETIC APPLICATOR

[75] Inventors: James J. Heneghan, North Granby; Leonard E. Hesse, Gilford, both of Conn.

[73] Assignee: LIS Corporation, Ansonia, Conn.

[21] Appl. No.: 09/078,061

[22] Filed: May 12, 1998

[51] Int. Cl.$^6$ .................................................. B25G 3/00
[52] U.S. Cl. ........................... 132/200; 300/20; 300/21; 425/DIG. 29
[58] Field of Search .............................. 132/200; 300/20, 300/21; 19/145.3; 425/515, 383, 111, DIG. 29

[56] References Cited

U.S. PATENT DOCUMENTS

| | | |
|---|---|---|
| 29,099 | 7/1860 | Power . |
| 188,227 | 3/1877 | Bacon . |
| D. 206,641 | 1/1967 | Hill ......................................... D83/12 |
| D. 251,013 | 2/1979 | Kettel ........................................ D24/8 |
| D. 269,811 | 7/1983 | Kaufman . |
| D. 270,762 | 9/1983 | Kaufman . |
| D. 336,955 | 6/1993 | Hadaway ............................... D24/100 |
| D. 373,238 | 9/1996 | Taylor et al. ............................. D28/7 |
| 467,599 | 1/1892 | Abundi et al. . |
| 532,359 | 1/1895 | Bradley . |
| 982,232 | 1/1911 | Bartholomew . |
| 1,345,280 | 6/1920 | Sweet . |
| 1,498,215 | 6/1924 | Vidaver . |
| 1,687,674 | 10/1928 | Lawson . |
| 1,857,145 | 9/1932 | Funk . |
| 2,218,738 | 10/1940 | Boysen et al. ............................ 132/84 |
| 2,346,782 | 4/1944 | Piluso ...................................... 300/21 |
| 2,491,274 | 12/1949 | McNeill ................................. 128/269 |
| 2,510,490 | 6/1950 | Ager ...................................... 128/269 |
| 2,735,167 | 2/1956 | Olsen ...................................... 29/433 |
| 2,810,150 | 10/1957 | Ellman ..................................... 15/244 |
| 2,903,914 | 9/1959 | Tarzian ..................................... 74/820 |
| 2,932,277 | 4/1960 | Borah .................................... 118/270 |
| 3,126,006 | 3/1964 | Dowell .................................. 128/356 |
| 3,228,398 | 1/1966 | Leonard et al. ....................... 128/269 |
| 3,242,519 | 3/1966 | Murray .................................... 15/244 |
| 3,405,437 | 10/1968 | Murray .................................... 29/450 |
| 3,798,736 | 3/1974 | Gibbons et al. ...................... 29/208 F |
| 3,847,151 | 11/1974 | D'Alessandro et al. ............... 128/269 |
| 3,951,460 | 4/1976 | Blankschein ............................. 300/21 |
| 4,100,717 | 7/1978 | Kontinen ................................. 53/138 |
| 4,163,142 | 7/1979 | Descovich et al. ...................... 219/79 |
| 4,253,452 | 3/1981 | Powers et al. .......................... 128/152 |
| 4,398,327 | 8/1983 | Yamazaki .............................. 29/33 R |
| 4,401,130 | 8/1983 | Halford et al. ....................... 132/88.5 |
| 4,543,702 | 10/1985 | Wada ....................................... 29/434 |
| 4,746,238 | 5/1988 | Levine .................................. 401/196 |
| 4,767,398 | 8/1988 | Blasius, Jr. ............................... 604/1 |
| 4,838,851 | 6/1989 | Shabo ....................................... 604/1 |
| 4,856,136 | 8/1989 | Janssen ................................. 15/244.3 |
| 4,887,994 | 12/1989 | Bedford .................................... 604/1 |
| 4,913,682 | 4/1990 | Shabo ....................................... 604/1 |
| 4,934,011 | 6/1990 | Haug ........................................ 15/145 |
| 4,935,001 | 6/1990 | George ..................................... 604/1 |
| 5,003,660 | 4/1991 | Oohinata et al. ..................... 15/244.1 |
| 5,085,633 | 2/1992 | Hanifl et al. ............................ 604/35 |
| 5,123,431 | 6/1992 | Wilson ................................... 132/320 |
| 5,158,532 | 10/1992 | Peng et al. ............................... 604/1 |
| 5,212,847 | 5/1993 | Melcher et al. ...................... 25/244.1 |
| 5,358,480 | 10/1994 | Melcher et al. .......................... 604/1 |
| 5,542,144 | 8/1996 | Forsline .................................. 15/188 |

FOREIGN PATENT DOCUMENTS

NR 130170   3/1901   Germany .

*Primary Examiner*—Todd E. Manahan
*Attorney, Agent, or Firm*—St. Onge Steward Johnson & Reens LLC

[57] ABSTRACT

A cosmetic applicator is disclosed which includes an applicator pad, or tip, comprised of a single piece of foam rubber having a substantially uniform thickness. An elongated handle, or wand, having at least one threaded end is positioned inside an opening in the applicator pad. An adhesive, inside the opening of the applicator pad, attaches the applicator pad to the threaded end of the handle. Notably, the adhesive may be inserted into the opening of the applicator pad during the assembly process and, most advantageously, it does not require drying for further handling. The method for making the applicator for applying cosmetics generally comprises placing an applicator tip in tension, forming a cavity in the applicator tip, and inserting a wand into the cavity.

24 Claims, 5 Drawing Sheets

METHOD OF MANUFACTURING A COSMETIC APPLICATOR

FIELD OF THE INVENTION

The present invention relates to applicators that may be used to apply cosmetics, medicine or the like.

BACKGROUND OF THE INVENTION

Cosmetic applicators comprising a wand, or handle, formed by injection molding and having a foam tip attached to one end of the handle are known. The tip is usually made of two pieces of foam rubber which are heat sealed together. When the pieces of foam are heat sealed, a hard ridge forms therealong. Disadvantageously, this hard ridge can be irritating to sensitive areas of skin, such as the area around the eyes.

Conventional applicators have other undesirable characteristics in that the handle tends to disconnect from the foam tip, sometimes termed the sponge portion, due to deterioration of the adhesive after use or when it is used in a rough manner. There are generally two types of connecting means which give rise to this problem. In one type of connecting means, adhesive is applied to one end of the handle and then the handle is inserted into an opening between the pair of sponge pieces so that it is adhered to them. In the other type, the applicator may be made by preforming a sponge block then plunging the handle into it. Both types of applicator connecting means are disadvantageous.

Several patents attempt to address the aforementioned deficiencies of the prior art, i.e., the undesirable disconnection of the tip from the wand. For example, U.S. Pat. No. 4,746,238 to Levine discloses a handle having helical ribs formed at the handle end. Fibrous material is evenly deposited over the ends and assumes the shape of the ribbed ends. Disadvantageously, the exterior surface of the applicator, where the fibrous material is deposited, is uneven. Thus, the exterior surface is not smooth and the cosmetic medium deposited in the crevasses can not be applied to the intended area and therefore is wasted.

U.S. Pat. No. 5,003,660 to Oohinato et al. discloses a core rod and a sponge portion at an inner end of the core rod. The sponge portion is molded integral with the core rod and then subjected to foaming. The sponge portion is provided with disconnection preventive means at the inner end of the core rod; the disconnection preventive means is coated with a rubber film so that the sponge portion is firmly connected to the core rod via the rubber film. Despite its asserted advantages, the patentee admits that the design is undesirable because the tip portion "is liable to be disconnected from the core rod due to a low magnitude of resistance between the core rod and the sponge portion when it is designed in smaller dimensions as is the case with a . . . small-sized applicator." U.S. Pat. No. 5,003,660, Col. 1, lines 42–46 (emphasis added). The Oohinato et al. method of manufacture is also undesirable if the sponge portion material is prefabricated prior to applicator assembly.

Figure 11:
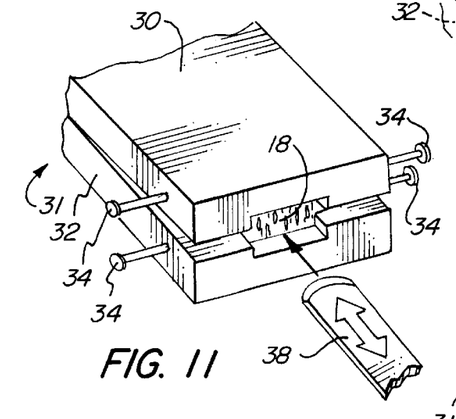

U.S. Pat. No. 2,932,277 to Borah discloses a moistening device. FIG. 11 illustrates a screw threaded fastener with a central stem having spiral grooves resembling a screw head, which holds the sponge in place and prevents it from becoming displaced from the receptacle while it is being used. In addition, the Borah patent shows that the screw is flat. The Borah patent is disadvantageous, however, because the foam tip does not completely surround the screw; thus, the exposed screw could cause injury if it came into contact with sensitive areas, such as the sensitive skin of the eyes.

U.S. Pat. No. 2,491,274 to McNeill discloses an applicator tip made of a single piece of synthetic foam having a non-uniform thickness. Col. 2, lines 50–52; and Col. 3, lines 9–13. The applicator wand has, for example, projections which engage the applicator tip and secure it to the wand. The shape of the McNeil applicator tip and wand, however, could make manufacturing difficult due to the non-uniformity of the tip and the shape of the preferred wand head.

Also a source of difficulty is how to assemble in mass production a cosmetic applicator made from a solid piece of foam. The difficult arises when a cavity in a foam applicator tip is attempted to be created because foam is a flexible material. A foam tip has a tendency to compress when a cutting tool is pressed against the tip which may result in either the creation of a non-uniform cavity or no cavity at all.

U.S. Pat. No. 4,401,130 to Halford, et al. discloses a swab article having a bore in the body of the swab. The bore is created by a rotating, hollow cylindrical tool. The cylindrical tool may not, however, be effectively used to create an appropriate cavity for a wand end having a flat head.

U.S. Pat. No. 5,212,847 to Melcher et al. discloses a swab and method of manufacturing. Melcher et al. discloses that if the pad portion is formed without a slit, then the slit can be formed with a hand operated knife, a movable blade or burned with a hot electrode. A hand operated knife and a movable blade, however, may have the disadvantage with creating a cavity as described above. Similarly, the use of a hot electrode on a cosmetic applicator tip may be disadvantageous because it may leave unsightly hard ridges.

What is desired, therefore, is an applicator comprising a wand having an attached tip, wherein the tip is reliably secured to the wand without disconnection even after extended and rough use, wherein the tip is made so that it does not have any hard ridges that could irritate the user, wherein the tip completely surrounds one end of the wand, wherein the tip is also attached to the wand by an adhesive which is applied during the assembly process which does not require drying for further handling, wherein the applicator is inexpensive to manufacture and can be quickly and easily assembled.

SUMMARY OF THE INVENTION

Accordingly, it is an object of the present invention to provide a cosmetic applicator having a tip and a wand, wherein the tip is reliably secured to the wand and does not disconnect even after prolonged or rough usage.

It is another object of the present invention to provide a cosmetic applicator of the above character having a tip having a smooth and seamless outer surface which is not irritating to the user.

It is still another object of the present invention to provide an applicator of the above character wherein the tip is made of a single piece of foam rubber having a uniform thickness.

It is still a further object of the present invention to provide a cosmetic applicator of the above character which is inexpensive to manufacture and which can be quickly and easily assembled.

It is yet another object of the present invention to provide a method of making a cosmetic applicator wherein the foam tip can be attached to a wand in a continuous, mass production fashion.

It is another object of the invention to provide a cosmetic applicator of the above character wherein the tip is attached to the wand via a threaded wand end and an adhesive which is applied during the assembly process to permit the assembled wand and tip to be handled prior to the adhesive drying.

To overcome the deficiencies of the prior art and to achieve the objects and advantages listed above, an applicator for the application of a cosmetic medium and the like is disclosed which comprises a wand, or handle, having at least one threaded end and a tip, made from a single piece of foam rubber, preferably latex foam rubber, and having an interior cavity with an open-end mouth. The threaded end of the wand is positioned substantially in the interior cavity of the tip and extends rearwardly therefrom. An adhesive is inserted at least partially inside the interior cavity of the tip and secures the tip to the threaded end of the wand.

A semi-automated method of manufacturing the applicator is also disclosed and comprises the following steps. First, a plurality of foam rubber tips are simultaneously cut from a single sheet of polymeric foam, preferably latex foam rubber. Second, the latex foam tips are positioned on a motorized turntable. The turntable rotates to a station where a slit is cut into the foam head. Then, the turntable rotates to a station where a handle, or wand, with a helically threaded screw head having adhesive applied to it is inserted and rotated into the slit.

The applicator of the present invention has two important features which are advantageous over the prior art. The first feature is the tip, which is comprised of a single piece of foam rubber. Because the tip is made of a single piece of foam rubber, it is seamless, i.e., the outer surface of the tip is smooth and has no rough edges which could cause discomfort to a user when using the applicator on sensitive areas of the skin. This is in contrast to the prior art applicators, wherein two pieces of foam, usually urethane foam, are heat sealed together, resulting in a hard ridge about the circumference of the pad.

The second advantageous feature of the applicator of one embodiment of the present invention is the threaded portion of the handle. It sufficiently engages the applicator pad and secures the pad to the handle so that the applicator may be handled, packaged and shipped before the adhesive completely dries. This is unlike conventional manufacturing processes, wherein the adhesive must dry before the applicator can be handled. Thus, many more applicators can be manufactured in a unit of time when compared to conventional applicator manufacturing processes. Once the adhesive dries, the tip is held onto the wand by the adhesive and the threads.

The invention and its particular features and advantages will become more apparent from the following detailed description when considered with reference to the accompanying drawings.

DETAILED DESCRIPTION OF THE DRAWINGS

An applicator 10 for applying cosmetics, medicine and the like is shown in FIGS. 1–5. It should be noted that for the sake of clarity all the components and parts of applicator 10 may not be shown and/or marked in all the drawings. As used in this description, the terms "front," "back," "top," "bottom," etc. refer to applicator 10 when in the orientations illustrated in FIGS. 1–5.

Applicator 10 is designed to apply cosmetics, but can carry any suitable medium. Reference to the applicator as a cosmetic applicator is exemplary only and is not intended to be limiting.

Figure 1:
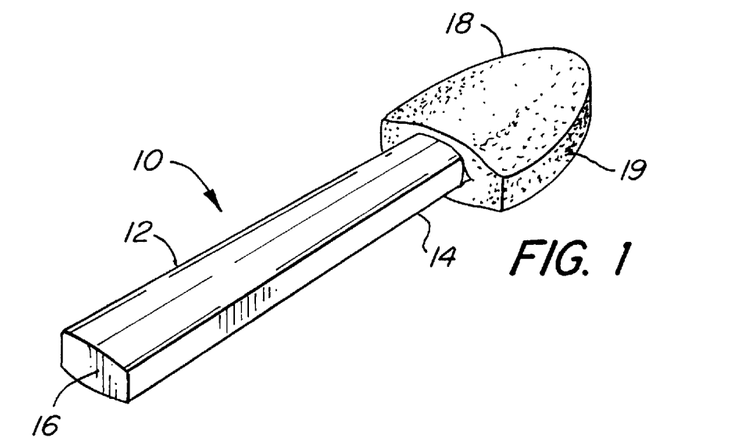
FIG. 1 is a front isometric view of an applicator constructed in accordance with the present invention.
Figure 2:
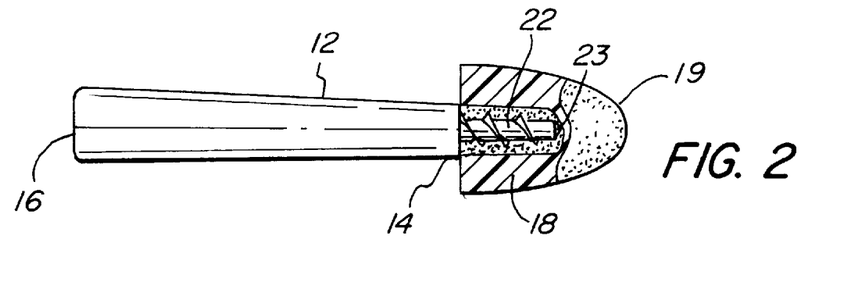
FIG. 2 is a front view of the first embodiment of the applicator with a partial cutaway of the applicator tip.
Figure 3:
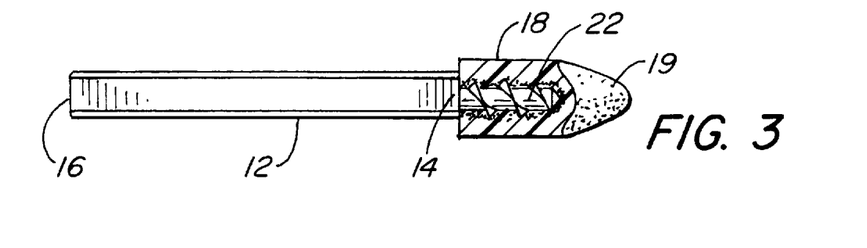
FIG. 3 is a side view of the first embodiment of the applicator shown in FIG. 2 with a partial cutaway of the applicator tip.
Figure 4:
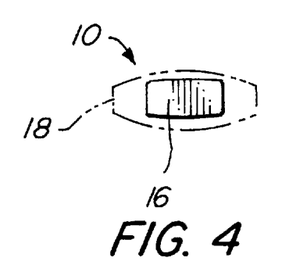
FIG. 4 is a bottom view of a wand of the applicator shown in FIG. 1.
Figure 5:
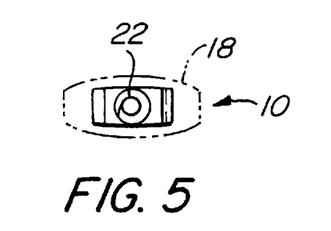
FIG. 5 is top view of a wand of the applicator shown in FIG. 1.

As illustrated in FIGS. 1–3, an applicator 10 comprises a wand or handle 12 having two ends 14, 16 and a tip 18 attached at one end 14. Adhesive 20 is one of the means used to secure the tip 18 to the end 14 of the wand 12, as discussed in more detail hereinbelow.

The wand or handle 12 is made of any suitable non-corrosive material, such as plastic, glass, wood or any suitable metal or other material having sufficient rigidity for its intended purpose. Any suitable method of manufacturing the wand 12 may be used. Most preferably, the wand 12 is made of plastic formed by injection molding.

As used herein, the terms "wand" and "handle" designate any elongated, stem-like piece of material. The rigidity or stiffness of the wand or handle 12 may vary with its intended usage, such as the medium it is intended to carry.

The wand 12 has at least one end 14. In the first embodiment of the cosmetic applicator, shown in FIGS. 2 and 3, the applicator wand has a threaded end. The threaded wand end 22 has a helical rib and a substantially flat head 23, which is covered by the foam rubber tip 18. This flat head prevents persons using the applicator 10 from being injured should the applicator 10 be applied too forcefully.

Figures 12, 13:
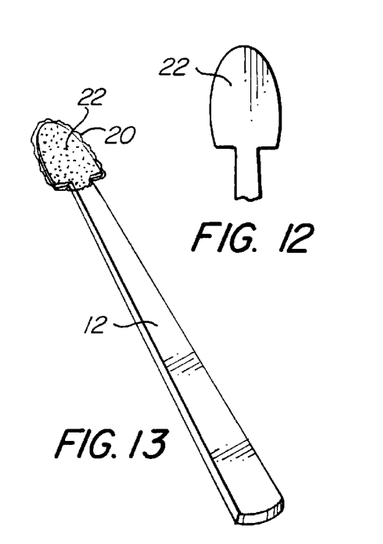
Figure 14:
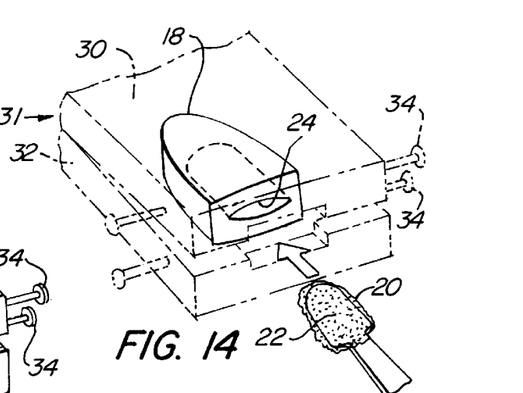

In the second embodiment of the cosmetic applicator, shown in FIGS. 12–14, the applicator wand has a flat head. Most preferably, the cosmetic applicator has a flat head and uses the thermoplastic attachment as described below.

The tip 18, also termed an applicator sponge or pad, is made of any suitable foam rubber, but is preferably made of latex foam rubber. The tip 18 may be formed into any shape, but preferably it is somewhat elongated and sized sufficiently so that it is not only well suited to fit one end 14 of the wand 12 but is also suitably shaped for applying cosmetics or other media to the skin.

The adhesive 20 can be either an adhesive generally used by manufacturers or can be a hypoallergenic thermoplastic material attachment that, when heated, seeps into the open cells of the tip 18 and creates an attachment after the thermoplastic cools. When the thermoplastic material is melted during assembly, it flows into the open cells 17 of the foam material of the tip 18. When the thermoplastic cools to a solid material, the thermoplastic is embedded in the foam cells 17 of the applicator tip providing an effective attachment between the applicator tip 18 and the wand 12. An advantage to using a thermoplastic material is that it cools and solidifies quicker than most adhesives.

The thermoplastic material used to attach the applicator tip 18 and the wand 12 must have a melting temperature between the temperature of hot water ordinarily found in a residential home, about 140 degrees Fahrenheit, and the melting temperature of the wand 12, approximately 180 degrees Fahrenheit. The melting temperature of a latex applicator tip 18 is greater than 250 degrees Fahrenheit. The thermoplastic material can be a material such as polypropylene, acrylic, styrene, cellulosic, vinyl, nylon or a fluorocarbon so long as its melting temperature is approximately between 140 and 180 degrees Fahrenheit, the melted material can migrate through an applicator tip to create an attachment, and the material is hypoallergenic. The preferred type of thermoplastic is Dexter EVA Polyshot Coolmelt, which is a hot melt glue.

Figure 6:
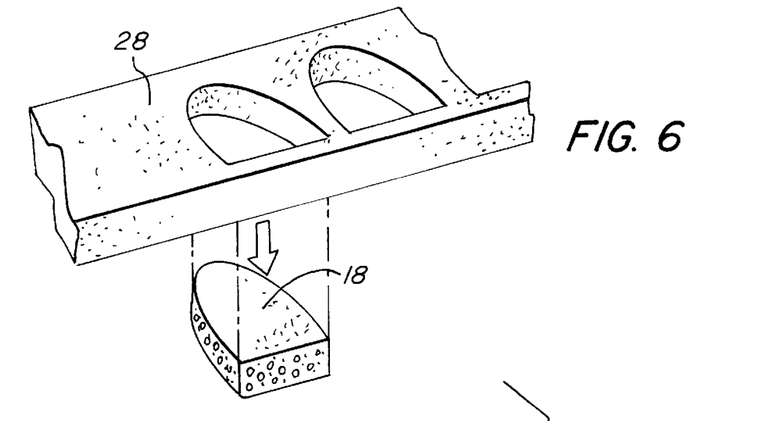
FIGS. 6–15 are schematic views showing the method of assembling the cosmetic applicator.
Figure 7:
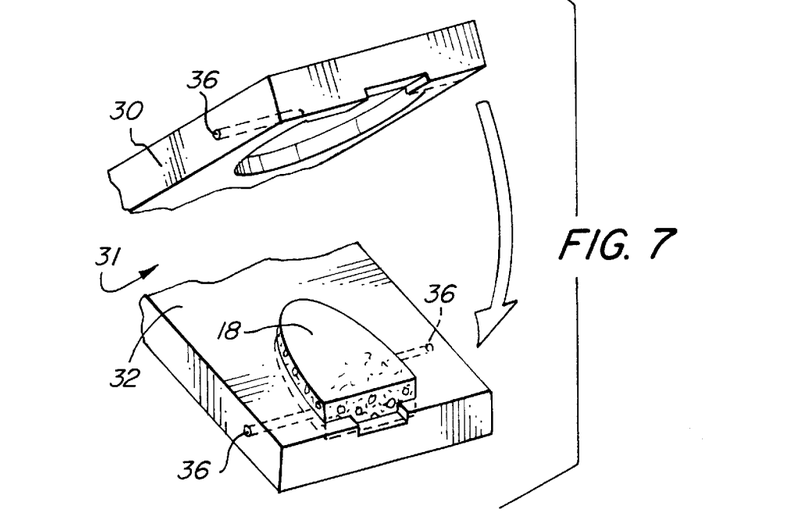

Preferably, the tip 18 is stamped from a single piece of foam rubber 28 of substantially uniform thickness, as shown in FIG. 6, and sized to cover the threaded end 22 of the wand 12. Most preferably, the tip 18 is about one-half to about three-quarters centimeters in width. Because of its construction from a single piece of latex foam rubber, the tip 18 has an outer surface which is substantially smooth. This design is more advantageous than the design of conventional applicator tips. As discussed earlier, applicator tips of the prior art are generally made of two pieces of urethane foam which are heat sealed together; a hard ridge forms therealong, which can be irritating to a user's sensitive skin areas. In contrast, the tip 18 of the present invention 10 has no hard ridges because there is no need to heat seal two pieces of foam rubber together. Thus, the tip 18 is less irritating to a user. The edges 19 may be ground smooth or to any desired shape.

Figure 8:
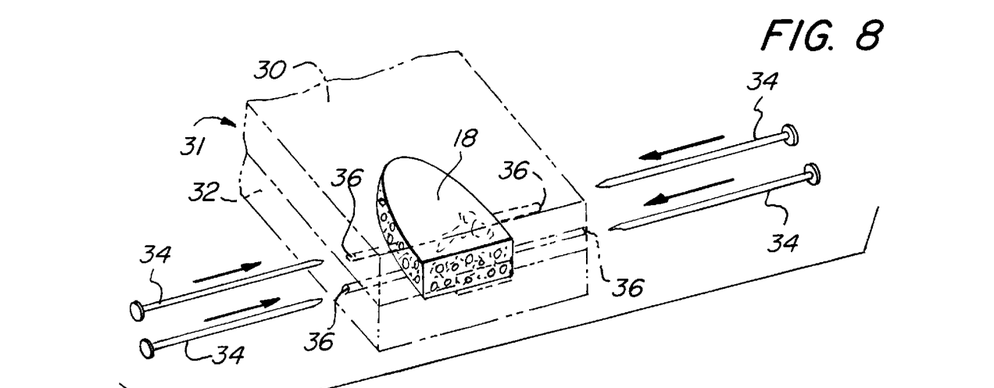
Figure 9:
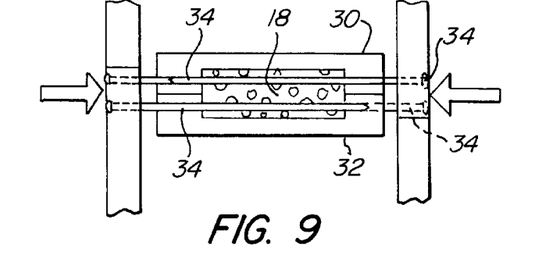

A method of manufacturing applicators in accordance with the present invention, which generally comprises the following steps, is illustrated in FIGS. 6–15. First, as shown in FIG. 6, a plurality of applicator tips 18 are formed from a single piece of latex foam rubber 28. As shown in FIG. 9, each applicator tip is individually placed within a bottom half 32 of a mold 31 which also has a top half 30. The interior of the mold 31 is fitted to the shape of the applicator tips 18. The top half 30 of the mold 31 is closed upon the bottom half 32 so that the applicator tip 18 is fitted inside the mold 31.

Figure 10:
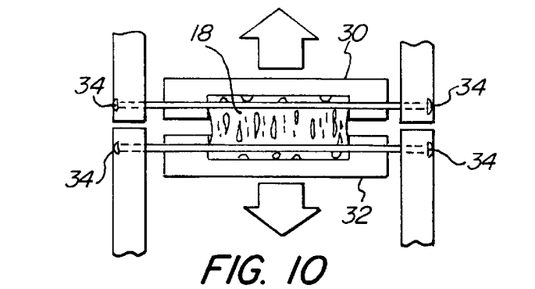

Next, as shown in FIGS. 8 and 9, four pins 34 are then slid into four pinholes 36 within the mold 31, two pinholes 36 being in each the top half 30 and the bottom half 32 of the mold 31. The four pins 34 pierce the applicator tip 18 such that two pins 34 are closer to the front of the applicator tip 18 and two pins 34 are closer to its back. Next, the bottom half 32 of the mold 31 is then pulled away a small distance from the top half 30 such that the pins 34 pull the front face of the applicator tip 18 away from the back face as shown in FIG. 10. Alternatively, the pins 34 could be arranged to pull one side of the tip 18 away from the opposing side. A slit 24 is then formed in the applicator tip 18 by inserting a cutting tool 38 into the applicator tip 18 while the top 30 and bottom 32 halves of the mold 31 are separated as shown in FIG. 11. A wand end 22 having an adhesive 20 applied to it, shown in FIGS. 12 and 13, is inserted into the slit 24 of the applicator tip 18. The applicator 10 is then ready to be removed from the mold 31.

Advantageously, when either a wand with a threaded end 22 with adhesive or a flat head 22 having thermoplastic attachment is used, the assembled applicator 10 does not require curing or drying for further handling. Thus, more applicators 10 may be produced per unit of time because one does not have to wait for the adhesive 20 or thermoplastic to dry.

Figure 15:
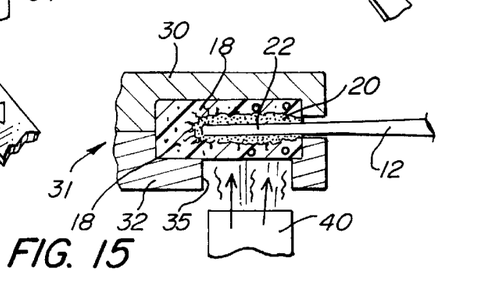

A heating device 40 can be employed, however, if the drying or curing time is desired to be faster or if heat is a required part of the attachment process. FIG. 15 shows a heating device heating the applicator tip 18, the wand 12 and the adhesive 20 through an opening 35 in the bottom mold 32.

Figure 16:
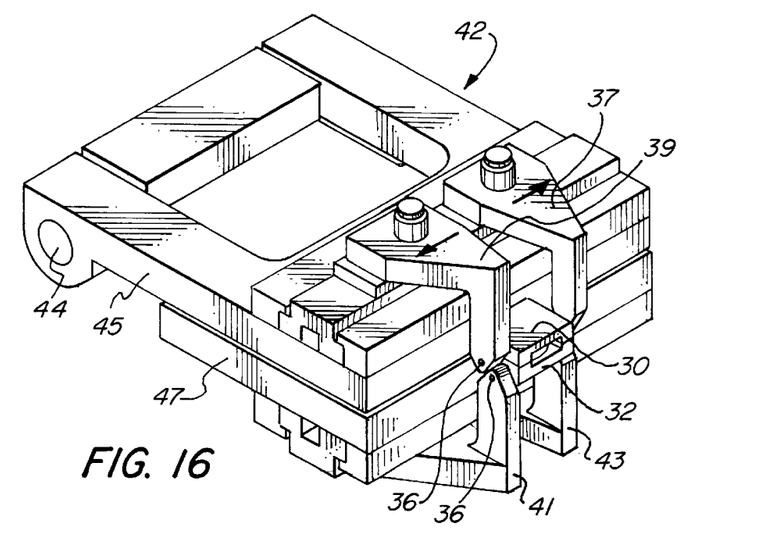
FIG. 16 is a front isometric view of the mold assembly used for the method of assembly shown in FIGS. 6–15.
Figure 17:
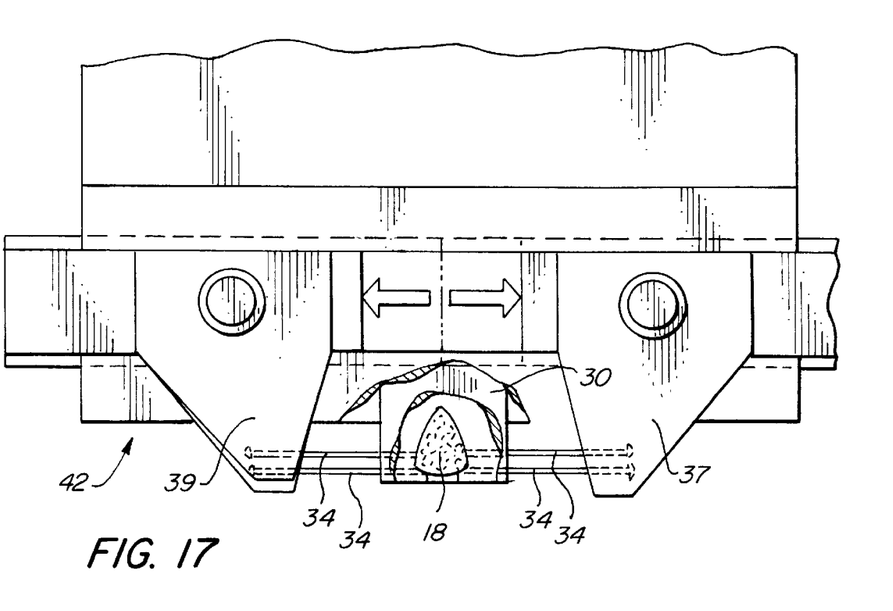
FIG. 17 is a top view of the mold assembly shown in FIG. 16 having a partial cutaway of the top half of the mold.

The preferred embodiment for the jig to assemble the applicator tip is a mold assembly 42, shown in FIGS. 16 and 17, which contains the upper 45 and lower 47 mold housings, mold 31, pins 34 and pin holders 37, 39, 41, 43. The upper 45 and lower 47 mold housings are connected by a hinge 44 and open and swing away from each other at the hinge 44. The top 30 and bottom 32 halves of the mold 31 are connected to upper 45 and lower 47 mold housings, respectively. Pin holders 37, 39, 41, and 42 each have a pinhole 36 to accept a pin 34. The left pin holders 37, 41 and the right pin holders 37, 43 can all move towards the mold 31 such that the pins 34 can pierce an applicator tip 18 in a mold 31, and move away from the mold 31 such that the pins 34 can be removed. The top 30 and bottom 32 halves of the mold 31 are replaceable so as to allow the molding apparatus 42 to hold different types of applicator tips 18 having different shapes.

Figure 18:
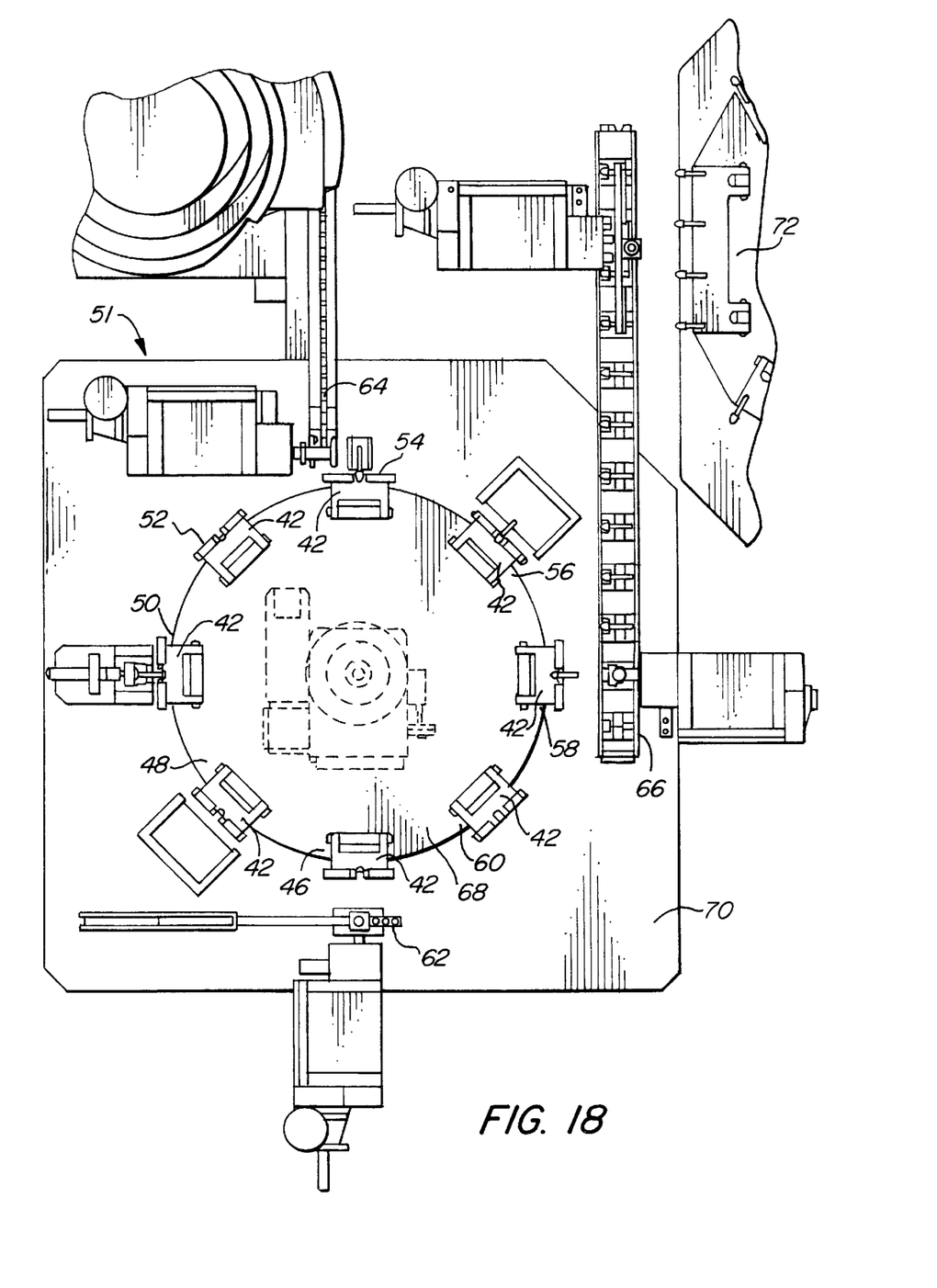
FIG. 18 is a top view of an assembly "line" assembling the applicator shown in FIG. 1 in accordance with the method shown in FIGS. 6–15.

The preferred embodiment of a revolving assembly line 51 is shown in FIG. 18. The assembly line 51 comprises a revolving round table 68 having eight mold assemblies 42, wherein one mold assembly 42 is affixed to the round table 68 at every one eighth of a revolution. The round table sits upon a larger table 70 having eight stationary stations: the loading station 46, the pin insertion station 48, the cut station 50, the first idle station 52, the insert handle station 54, the fuse glue station 56, the unload station 58, and the second idle station 60.

In operation, each mold assembly 42 beings the assembly process at the loading station 46, visits each station while rotating clockwise, and completes the assembly process at the unloading station 58. When a mold assembly 42 visits a station, either a process is completed upon the mold assembly 42 or the mold assembly 42 remains idle. The round table 68 then revolves around one eighth of a turn until each mold assembly 42 reaches its next station. This procedure is repeated until each mold assembly reaches the unloading station 58, which is the end of the assembly line 51. While the assembly line is active, all eight mold assemblies 42 are either undergoing a process or remaining idle.

The assembly procedure on the revolving assembly line begins with cutting out the applicator tips 18 from a sheet of latex foam 28. The applicator tips 18 are delivered to the assembly line 51 by the applicator tip conveyor 62. An applicator tip 18 is loaded into the mold assembly 42 at the loading station 46 by placing an applicator tip 18 in the bottom mold 32 and closing the top mold 30 onto the bottom mold 32.

After inserting an applicator tip 18 into the mold assembly, the round table 68 revolves clockwise to the pin insertion station 48. The pins of the mold assembly are pushed into the mold assembly which pierces the applicator tip 18 and holds it in place as shown in FIG. 9.

The mold assembly then revolves to the cut station 50. The bottom half 30 and top half 32 of the mold 31 are separated slightly such that the pins 34 exert a force upon the applicator tip 18 and stretch it as shown in FIG. 10. A cutting tool 38 is inserted into the applicator tip 18 as shown in FIG. 11 to create an opening 24 in the applicator tip 18.

After creating an opening, the mold assembly 42 rotates to a first idle station 52 in which no process is performed upon the mold assembly 42.

The mold assembly 42 then revolves clockwise to the insert wand station 52. The bottom half 30 and top half 32 of the mold 31 are still separated slightly such that the opening 24 is spread and made ready to receive a wand end 22. A pre-glued wand 12 is then taken from a wand conveyor 64 and the end 22 of the wand 12 is inserted into the opening 24 of the applicator tip 18 as shown in FIG. 14.

The mold assembly 42 then revolves to the fuse glue station 56. At this station, the glue 20 is dried or cured. The drying process can be accelerated by applying heat from a heating device 40 such as a hot air gun.

The mold assembly then rotates to the unload station 58. First, the pin holders 37, 39, 41, 43 are slid away from the mold assembly 42 to remove the pins 34 from the applicator tip 18. Next, the top half 30 of the mold 31 is separated from the bottom half 32 and the cosmetic applicator 10 is removed in its assembled state. The assembled cosmetic applicator 10 is placed upon a cosmetic applicator conveyor 66 which transports the applicators 10 to be handled or packaged. The tip 18 of the applicator 10 can be buffed or shaped at a buffing station 72.

The mold assembly 42 then rotates to a first idle station 52 in which no process is performed upon the mold assembly 42. The above procedure is then repeated beginning at the next station, the load station 46.

From the foregoing description, it can thus be seen that the applicator 10 of the present invention provides and inexpensive and yet highly effective swab that can be quickly, easily and inexpensively manufactured in a process that is almost entirely automated.

It should be understood that the foregoing is illustrative and not limiting and that obvious modifications may be made by those skilled in the art without departing from the spirit of the invention. Accordingly, reference should be made primarily to the accompanying claims, rather than the foregoing specification, to determine the scope of the invention.

What is claimed is:

1. A method for making an applicator for applying cosmetics and the like, comprising the steps of:
    placing an applicator tip in tension;
    forming a cavity in the applicator tip; and
    inserting a wand into the cavity.

2. A method according to claim 1, further comprising the steps of:
    releasing said tension from said foam; and
    adhering an end of said wand within said cavity to secure said tip to said wand.

3. A method according to claim 2, wherein the applicator tip is made from polymeric foam and the step of adhering comprises applying a thermoplastic material to said wand end and heating both the wand end and the foam subsequent to insertion of the wand end into the cavity to melt the thermoplastic and permit the thermoplastic to seep into the foam, and thereafter permitting the thermoplastic to cool to provide an adhesion between the foam and the wand end.

4. A method according to claim 2, wherein the step of adhering comprises:
    applying an adhesive to the wand end;
    inserting the wand end with the adhesive thereon into the cavity; and
    permitting the adhesive to cure to thereby adhere the applicator tip to the wand end.

5. A method according to claim 1, wherein the applicator tip is made from polymeric foam and has two opposed surfaces and wherein said step of placing an applicator tip in tension comprises grasping at least one of said two opposed surfaces and pulling said surface away from the other of said two surfaces to provide said tension.

6. A method according to claim 5, wherein said grasping is accomplished by inserting a first pair of pins into the tip adjacent one of the opposed surfaces and inserting a second pair of pins into the tip adjacent the other opposed surface and forcing said pins apart to provide tension on the tip.

7. A method according to claim 1, wherein said forming a cavity comprises:
    moving a cutting tool with a sharpened front edge linearly toward the tip to cut the applicator tip and provide said cavity; and
    removing said cutting tool while maintaining said pairs of pins in spaced apart relation and the applicator tip in tension to provide said cavity.

8. A method for according to claim 7, wherein said first pins are inserted laterally from one side of the applicator tip and said second pair of pins are inserted laterally from the other side of the applicator tip, and wherein said first pair of pins are in parallel relationship and said second set of pins are in parallel relationship, the first pair of pins moving in a relation parallel to the second pair of pins.

9. A method according to claim 8, wherein inserting the pins into the tip comprises:
    providing a mold having a top half, a bottom half and a plurality of holes to accept said pins;
    placing the applicator tip within the mold; and
    inserting the pins into the mold.

10. A method according to claim 9, wherein the top half and the bottom half of the mold can move apart from each other and wherein the step of forcing said pins apart to provide tension on the tip comprises moving the top half and the bottom half of the mold apart from each other to provide tension on the applicator tip.

11. A method for making an applicator for applying cosmetics and the like, comprising the steps of:
    providing an elongated wand having a handle portion and an end;
    providing an applicator tip comprising polymeric foam, said foam being elastically deformable, the tip having an end portion for receiving the wand and two opposed surfaces adjacent said tip end portion;
    applying forces to said opposed surfaces to elastically deform said foam and place it in tension;
    forming a cavity into said tip end portion while maintaining said foam in tension, said cavity having an interior wall; and
    inserting said wand end into said cavity.

12. A method according to claim 11, further comprising the steps of:
    releasing said tension from said foam; and
    adhering said wand end to said cavity wall to secure said tip to said wand.

13. A method according to claim 11, wherein said step of applying forces to said opposed surfaces comprises grasping at least one of said two opposed surfaces and pulling said surface away from the other of said two surfaces to provide said tension.

14. A method according to claim 13, wherein said grasping is accomplished by inserting a first pair of pins into the tip adjacent one of the opposed surfaces and inserting a second pair of pins into the tip adjacent the other opposed surface and forcing said pins apart to provide tension on the tip end portion.

15. A method according to claim 11, wherein said forming a cavity comprises:

moving a cutting tool with a sharpened front edge linearly toward the tip end portion to cut the foam and provide said cavity; and removing said cutting tool while maintaining said pairs of pins in spaced apart relation and said foam in tension to provide said cavity.

16. A method according to claim 15, wherein inserting the pins into the tip comprises:

providing a mold having a top half, a bottom half and a plurality of holes to accept said pins;

placing the applicator tip within the mold; and inserting the pins into the mold.

17. A method according to claim 16, wherein the top half and the bottom half of the mold can move apart from each other and wherein the step of forcing said pins apart to provide tension on the tip end portion comprises moving the top half and the bottom half of the mold apart from each other to provide tension on the tip end portion.

18. A method according to claim 16, wherein the mold further comprises a pin holder attached to each pin, the pin holder being movable with respect to the mold in the direction of the pin movement, wherein inserting the pins into the mold comprises moving the pin holder towards the applicator tip to insert the pins into the tip.

19. A method according to claim 11, wherein the step of adhering comprises applying a thermoplastic material to said wand end and heating both the wand end and the foam subsequent to insertion of the wand end into the cavity to melt the thermoplastic and permit the thermoplastic to seep into the foam, and thereafter permitting the thermoplastic to cool to provide an adhesion between the foam and the wand end.

20. A method according to claim 11, wherein the step of adhering comprises applying an adhesive to the wand end;

inserting the wand end with the adhesive thereon into the cavity; and permitting the adhesive to cure to thereby adhere the foam to the wand end.

21. A jig for assembling a cosmetic applicator, comprising:

a mold having two halves, said mold having an internal cavity for accepting an applicator tip, said two halves capable of separating from each other;

at least one pin holder each having a pinhole; and at least one pin for each pin holder, each pin for being accepted by a pin holder pinhole, for penetrating the applicator tip and for applying tension to the applicator tip when the two halves of the mold are separated.

22. The jig for assembling a cosmetic applicator according to claim 21, wherein said pins are fixed to their respective pin holder and wherein each pin holder is moveable in a direction longitudinal to a pin fixed to it such that the plurality of pins can be inserted into the mold by moving each pin holder towards the mold.

23. The jig for assembling a cosmetic applicator according to claim 22, wherein there are four pin holders each having one pin fixed to it and wherein two pins are for being inserted into a top half of the mold and the other two pins are for being inserted into a bottom half of the mold.

24. The jig for assembling a cosmetic applicator according to claim 21, further comprising a mold housing having an upper half and a lower half connected together by a hinge, the upper half of the mold and first and second pin holders being fixed to the upper half of the mold housing, the lower half of the mold and third and fourth pin holders being fixed to the lower half of the mold housing, the pins for applying tension on the applicator when the pins are inserted into the applicator tip and the upper and lower halves of the mold housing are separated by opening the hinge.

* * * * *